United States Patent [19]

O'Brien et al.

[11] 3,932,633

[45] Jan. 13, 1976

[54] NOVEL O-TRIAZENOBENZAMIDES, IN TREATING AGGRESSIVE BEHAVIOR

[75] Inventors: John Terence O'Brien, Chesire; Zaven S. Ariyan, Woodbury, both of Conn.

[73] Assignee: Uniroyal Inc., New York, N.Y.

[22] Filed: Mar. 4, 1974

[21] Appl. No.: 447,605

Related U.S. Application Data

[62] Division of Ser. No. 311,878, Dec. 4, 1972.

[52] U.S. Cl. .............................. 424/226; 260/140
[51] Int. Cl.² .................................... A61K 31/655
[58] Field of Search .................... 424/226; 260/140

[56] References Cited
UNITED STATES PATENTS

| | | | |
|---|---|---|---|
| 2,173,324 | 9/1939 | Schmelzer et al. | 260/140 |
| 2,828,299 | 3/1958 | Von Glahn et al. | 260/140 |
| 2,842,535 | 7/1958 | Lowenfeld et al. | 260/140 |
| 3,138,521 | 6/1964 | Jelinek et al. | 260/140 X |
| 3,162,571 | 12/1964 | Adams et al. | 260/140 X |
| 3,741,951 | 6/1973 | Hess et al. | 260/140 |

*Primary Examiner*—Stanley J. Friedman
*Attorney, Agent, or Firm*—Willard R. Sprowls, Esq.

[57] ABSTRACT

Certain o-triazenobenzamides are useful as anti-aggression agents. Certain methods of preparation are novel.

4 Claims, No Drawings

NOVEL O-TRIAZENOBENZAMIDES, IN TREATING AGGRESSIVE BEHAVIOR

This is a division of application Ser. No. 311,878, filed Dec. 4, 1972.

CROSS REFERENCE TO RELATED APPLICATIONS

This application is related to, and incorporates by reference, the contents of application Ser. No. 282,311, of Ariyan, filed Aug. 21, 1972.

BACKGROUND OF THE INVENTION

1. Field of the Invention

The neurochemistry of aggression has recently attracted much attention, since it has been recognized that aggressive behavior in animals and man can be produced by alterations in ordered brain function. In man, aggressive behavior is very often associated with almost every type of mental disease. Thus, aggression is a major side effect of most mental disorders.

This invention relates to a broad class of novel o-triazenobenzamides which are useful as psychotherapeutic agents, particularly as anti-aggression agents. Thus, certain of these o-triazenobenzamides have been found to be highly selective for the abolition of aggressive behavior at doses which cause little or no signs or symptoms of central nervous system depression or toxicity.

It is well accepted in neuropharmacology that there is no clear distinction between sedative-hypnotics and minor tranquilizers. Virtually all known minor tranquilizers which are effective in reducing anxiety also produce drowsiness, ataxia (inability to coordinate muscular movements), and sleep when given in larger doses. Virtually all sedative-hypnotic drugs in small doses are "anxiolytic" (causing apprehension or anxiety). Sedative hypnotics such as alcohol and short-acting barbiturates tend to produce behavioral excitation prior to promoting drowsiness and sleep. The sedative-hypnotics and minor tranquilizers produce discrete, predictable changes of behavior that can be applied to therapeutic advantage in neurotics. Aside from their ability to promote sleep, their major behavioral action of therapeutic advantage is their ability to slightly reduce the level of arousal-excitability, overcome passive avoidance (social withdrawal, suppressed or submissive behavior), slightly diminish aggressive hostility, and increase the response to environmental stimuli. The effect, for example, of a "psychomimetic" drug (inducing psychosis-like symptoms) on animal behavior, such as LSD in rats and cats, has been said to increase excitement and aggression.

Currently, aggressive behavior in mental disease patients is usually controlled by such major tranquilizers as chlorpromazine. This approach to the problem of controlling mental disorders is not entirely satisfactory since patients under the influence of this type of medication are overly depressed and have difficulty in satisfactorily returning to society and in functioning normally. Chlorpromazine is a strong central nervous system depressant, both in normal and schizophrenic patients. It has been the drug of choice for the treatment of so-called "back ward" schizophrenics, and is now used in out-patient therapy in cases of simple schizophrenia. The compound has many side effects, the most serious being that it causes depression at the same time that it alleviates the schizophrenic symptoms. It also is disadvantageous in that it is extremely toxic and has been known to cause liver damage and blood disorders.

The abolition of aggressive behavior in schizophrenics without neurotoxicity as characterized by depression would be a most desirable feature for a new drug in the therapy of mental disease. The o-triazenobenzamide compounds of the present invention have been found to selectively block aggressive behavior but without causing significant depression.

Accordingly, in one aspect, the invention is a broad class of novel o-triazenobenzamides. In another aspect, the invention is a method of treating aggressive behavior using these compounds. In yet another aspect, the invention is directed to psychotherapeutic pharmaceutical compositions comprising the novel o-triazenobenzamides. In a still further aspect, the invention is directed to methods of preparing the novel o-triazenobenzamides.

2. Description of the Prior Art

Triazene derivatives, including triazenobenzamide derivatives are, of course, known.

For example, Shealy et al, J. Pharm. Sci., 60, 1426 (1971) disclose 2-(3,3-dialkyl-1-triazeno)-benzamides (II) as anti-cancer agents which are related to their 5-(3,3-dimethyl-1-triazeno)-imidazole-4-carboxamide (III), a known anti-cancer compound. Lin et al, J. Med. Chem., 15, 201 (1972) also disclose 2-(3,3-dimethyl-1-triazeno)-benzamide as an anti-cancer agent. The triazeno group in the position ortho to the carboxamide on the benzene ring of these compounds shows a similarity to the novel o-triazenobenzamides of the present invention.

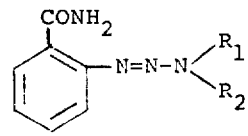

II

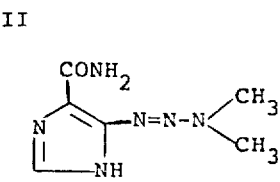

III

These disclosures are the only previous examples of o-triazenobenzamides. Ordinarily, when anthranilamide (IV) is diazotized with sodium nitrite in dilute aqueous hydrochloric acid, the intermediate o-carbamoylbenzenediazonium chloride (V) cyclizes to 1,2,3-benzotriazin-4(3H)-one, (VI), a known compound, the use of which is described in Ser. No. 282,311 of Ariyan mentioned above.

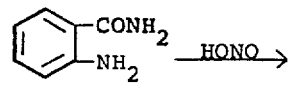

IV

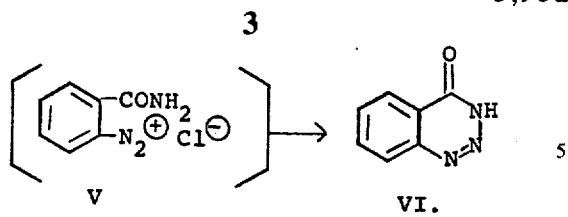

Shealy, however, succeeded in preparing and isolating the o-carbamoylbenzenediazonium tetrafluoroborate (VA) in place of the chloride, and this enabled them to couple the indicated diazonium compound with a number of dialkylamines to obtain their compounds (II):

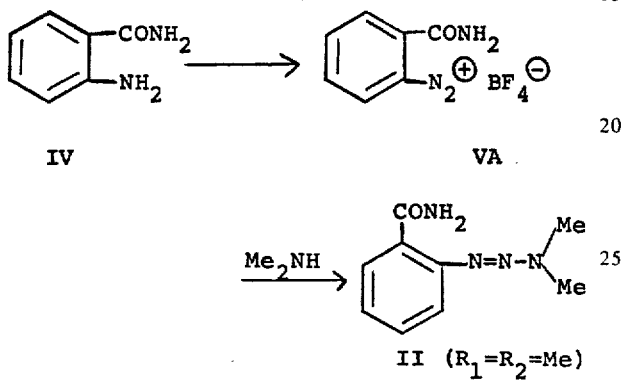

It is also known from Schulze, Ann., 251, 163 (1888) that when 3-aminobenzamide is diazotized under acid deficient conditions, 3,3'-diazoaminodibenzamide, an isomer of one of the present compounds, is produced. Derivatives of 3,3'-diazoaminodibenzamide have been reported by Julia et al, Bull. Soc. Chim. Fr., 376 (1968).

No reference, however, has reported the preparation of any o-phenyltriazenobenzamides.

Several examples of heterocyclic rings coupled to either an identical ring or to a benzene ring are well known, e.g., Mohr, Ber., 31, 3495 (1898) and Stark et al, Ber., 46, 2702 (1913); however, no reference has reported the preparation of any heterocyclic o-triazenobenzamides.

SUMMARY OF THE INVENTION

The present invention provides a broad class of novel compounds having psychotherapeutic activity in controlling aggressive behavior. These compounds are o-triazenobenzamides of the formula:

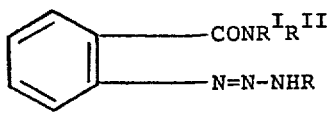

(A)

wherein R is (1) 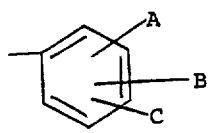

in which A and B are hydrogen and C is chloro, methyl, nitro, methoxy, ethoxy, carbamoyl or carboxymethyl; or A is hydrogen, B is chloro and C is methyl or methoxy; or
A is hydrogen and B and C are both methyl; or
A is hydrogen or methyl, B is nitro and C is methoxy;

(2) 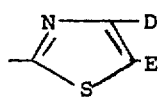

in which D is hydrogen or methyl and E is hydrogen or

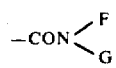

wherein F is hydrogen and G is phenyl, halophenyl or trimethylphenyl or benzyl; or F and G together with the nitrogen atom to which they are bonded, form a morpholine ring; or (3) pyridyl, halopyridyl, methoxypyridyl, quinolyl, anthraquinolyl or N-ethylcarbazolyl;

$R^I$ is hydrogen or methyl and $R^{II}$ is hydrogen, lower alkyl, phenyl or the sulfate of a dimethylamino lower alkyl group.

The novel compounds of the formula (A) actually exist in two tautomeric forms, which, for explanatory purposes are given below as formulae (Ia) and (Ib):

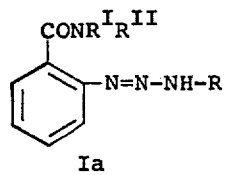

Ia

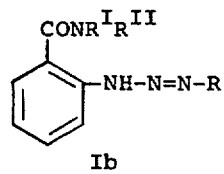

Ib

The tautomer (Ia), wherein R is, for example, phenyl is called 2-(3-phenyl-1-triazeno-benzamide, while tautomer (Ib) is called 2-(3-phenyl-2-triazeno)-benzamide. These tautomers are readily interconvertible, and any particular triazene may be either of the two tautomers or a mixture of both. For all unsymmetrically substituted triazenes this application will, therefore, use the nomenclature 2-(3-phenyl-1(or 2)-triazeno)-benzamide (R=phenyl) to describe the novel compounds.

The present invention also provides a method of controlling aggressive behavior in an animal subject without causing the central nervous system depression which is a typical side effect of drugs heretofore used to treat aggressive behavior. This is achieved by administering to an animal subject a therapeutically effective amount of at least one of the o-triazenobenzamides of the formula (A).

Generally, the amount of such o-triazenobenzamide that will be administered will be from about 0.1 to 250 mg/kg/day of body weight, preferably, from about 1 to 25 mg/kg/day. In humans, the amount will be from about 0.1 to 4 mg/kg/day.

The invention further provides new pharmaceutical compositions comprising at least one of the above specified o-triazenobenzamides of the formula (A).

Such pharmaceutical compositions comprise, in combination, a therapeutically effective amount of such an o-triazenobenzamide and a pharmaceutically acceptable carrier and/or diluent therefor.

For example, in the case of a tablet, the composition will comprise, in addition to the active ingredient, fillers, binders, and/or diluents such as lactose, methylcellulose, talc, gum tragacanth, gum acacia, agar, polyvinylpyrrolidone, stearic acid and corn starch. In the case of a liquid suspension for oral administration, the composition will comprise, in addition to the active ingredients, a filler such as sodium carboxymethylcellulose and/or a syrup, e.g., a glycerine based syrup. In the case of a parenteral solution or suspension, the composition will comprise the active ingredient and a suitable liquid solvent or dispersant such as a saline solution.

The above compounds of the formula (A) are prepared by novel methods and thus, the invention also provides methods for the preparation of the compounds of the invention.

According to the invention, compounds of the formula (A) are prepared by diazotizing an amine of the formula:

wherein R is as described above, to form an intermediate diazonium salt of the formula:

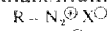

wherein $X^\ominus$ is an anion such as chloride or hydrogen sulfate. The diazonium salt is then coupled with an anthranilamide of the formula:

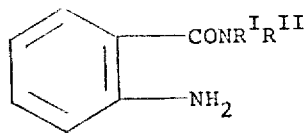

wherein $R^I$ and $R^{II}$ are as defined above, to yield a compound of the formula:

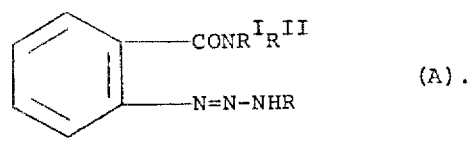

(A).

In some cases, it will be expedient to diazotize the anthranilamide in ethanolic fluoroboric acid rather than the amine and then couple the diazotized anthranilamide with the amine.

Various methods, some of which are novel, are employed in such diazotizations as follows:

Method A:

The amine is diazotized in dilute aqueous hydrochloric acid at about 0°C by the dropwise addition of aqueous sodium nitrite. The solution of the diazonium chloride is then neutralized with sodium acetate (pH4 – 5) followed immediately by the addition of the anthranilamide to the vigorously stirred solution. This method is applicable to anilines including nitroanilines, to heterocycles with a fused benzene ring substituted with the amino group, and to several heterocyclic amines forming stable aqueous diazonium chlorides.

Method B:

The amine is diazotized in glacial acetic acid or a 50% v/v mixture of propionic acid and acetic acid containing 10% concentrated sulfuric acid at 5° – 10°C by portionwise addition of dry, solid sodium nitrite. The solution of the diazonium salt is filtered into a vigorously stirred suspension of the anthranilamide in aqueous sodium acetate solution. This modification to the method is applicable to most heterocyclic amines with the exception of those aminothiazoles of the formula (A) wherein G is phenyl, halophenyl or trimethylphenyl.

Method C:

The amine is diazotized in glacial acetic acid or a 50% v/v mixture of propionic acid and acetic acid containing 5 – 10% sulfuric acid at 5° – 20°C by the dropwise addition of isoamyl nitrite. The diazonium salt is then treated as described in Method B. This modification of the method is applicable to heterocyclic amines including those for which Method B is not suitable.

Method D:

For the self coupling of anthranilamide, diazotization is performed at about 0°C, in tetrahydrofuran containing a catalytic amount of trichloroacetic acid, by the addition of isoamyl nitrite.

Method E:

In those cases where the amine is difficult to diazotize or forms an unreactive diazonium salt, the diazonium tetrafluoroborate derived from the anthranilamide is coupled with the amine in ethanol at room temperature.

Preparative examples representative of each of these methods will be given below.

DETAILED DESCRIPTION OF THE INVENTION

The compounds of the present invention are prepared according to the methods described above by diazotizing an aromatic or heterocyclic amine and coupling the diazonium salt with an anthranilamide, or in some cases, by diazotizing an anthranilamide and coupling the diazonium salt with an aromatic or heterocyclic amine.

There will now follow working examples showing the preparation of some of the compounds according to the invention using one or more of the above-described modifications of the method of the invention.

EXAMPLE 1 (Method D):

Preparation of 2,2'-diazoaminobenzamide

To 13.6 gm (0.10 mole) of anthranilamide dissolved in 100 ml. of tetrahydrofuran, a catalytic amount (0.1 – 0.2 gm.) of trichloroacetic acid was added. The solution was stirred in an ice-bath while 22 ml. (0.16 mole) of isoamyl nitrite were slowly added. The reaction was then transferred to a water bath at room temperature. After 1 hour, a yellow product precipitated. This product was filtered off, washed with ethanol and then ether, and air dried. Yield: 8.5 gm. (60% of theoretical). The solid was recrystallized from dimethylformamide and washed with ethanol and ether. m.p. 217°–218°C. (dec.).

EXAMPLE 2 (Method B):

Preparation of 2-[3-(2-thiazolyl)-2(or 1)-triazeno]-benzamide to 10.0 gm. (0.10 mole) of 2-aminothiazole dissolved in 100 ml. of glacial acetic acid to which 10 ml. of concentrated sulfuric acid had been added, 6.9 gm. (0.10 mole) of dry solid sodium nitrite were added portionwise, while the solution was stirred in an ice bath. The reaction mixture was filtered into a stirred suspension of 13.6 gm. (0.10 mole) anthranilamide in an aqueous solution of 21 gm. of sodium acetate in 100 ml. water. The yellow-brown precipitate was filtered off, washed with ethanol, dissolved in hot ethanol, charcoaled with Norit A, filtered, and permitted to crystallize on cooling. Yield: 12.0 gm. (50% of theoretical). The yellow solid was recrystallized from ethanol.

(Method C):

Alternatively, 15 ml. of isoamyl nitrite (0.11 mole) were added instead of sodium nitrite. The product obtained was somewhat less black in crude yield, and the overall yield was also 12 gm. m.p. 181°– 182°C. (dec.).

EXAMPLE 3 (Method A):

Preparation of 2-[3-(3-chloro-4-methylphenyl)-1(or 2)-triazeno]-benzamide

To 14.15 gm. (0.10 mole) of 3-chloro-4-methylaniline dispersed in 100 ml. of 3N hydrochloric acid, 7.0 gm. (0.10 mole) of sodium nitrite in 25 ml. of water were added dropwise, while the solution was stirred at about 0°C in an ice bath. The reaction mixture was then neutralized to pH 4 – 5 with 21 gm. of sodium acetate, and 13.6 gm. (0.10 mole) of anthranilamide were quickly stirred into the solution. The yellow precipitate was filtered off, and washed with a minimal amount of ethanol, then ether and petroleum ether. The solid was recrystallized from ethanol to give 18 gm. of yellow crystals. Yield 62%. m.p. 185°– 186.5°C. (dec.).

EXAMPLE 4 (Method A):

Preparation of 2-[3-(9-ethyl-3-carbazolyl)-2(or 1)-triazeno]-benzamide

To 10.5 gm. (0.05 mole) of finely divided 3-amino-9-ethylcarbazole dispersed in 50 ml. of 3N hydrochloric acid at about 0°C, 3.5 gm. (0.05 mole) of sodium nitrite in 15 ml. of water were added dropwise. The reaction mixture was filtered into a stirred suspension of 6.8 gm. (0.05 mole) of anthranilamide in an aqueous solution of 10.5 gm. of sodium acetate in 50 ml. of water. The solution was immediately filtered and let stand until precipitation had occurred. The precipitate was filtered off and washed with a minimal amount of ethanol, and then ether. The obtained yellow solid (2 gm.; 11% yield) was recrystallized from ethanol. m.p. 192.5°–193°C. (dec.).

EXAMPLE 5 (Method B):

Preparation of 2-[3-(4-methyl-5-morpholinocarbonyl-2-thiazolyl)-2(or 1)-triazeno]-benzamide To 5.0 gm. (0.022 mole) of 2-amino-4-methyl-5-morpholinocarbonyl thiazole dissolved in 20 ml. of glacial acetic acid to which 2ml. concentrated sulfuric acid had been added, 1.5 gm. (0.022 mole) of dry solid sodium nitrite were added portionwise, while the solution was stirred in an ice bath. The reaction mixture was poured into a stirred suspension of 3.0 gm. (0.022 mole) of anthranilamide in an aqueous solution of 8.4 gm. of sodium acetate in 100 ml. of water. The precipitate was filtered off, washed with ethanol and ether, and recrystallized from ethanol and petroleum ether to obtain 1 gm. (12% Yield) of a product having a m.p. of 187.5°– 188°C. (dec.)

EXAMPLE 6 (Method C):

Preparation of 2-[3-(4-methyl-5-(N-benzyl-carbamoyl)-2-thiazolyl)-2(or 1)-triazeno]-benzamide To 50 gm. (0.20 mole) of 2-amino-4-methyl-5-(N-benzylcarbamoyl)-thiazole dissolved in 200 ml. 50% v/v propionic acidglacial acetic acid and 20 ml. concentrated sulfuric acid, stirred in an ice bath, 30 ml. of isoamyl nitrite were added. The reaction mixture was poured into a stirred suspension of 27.2 gm. (0.20 mole) anthranilamide in an aqueous solution of 84 gm. sodium acetate in 1 liter of water. The orange precipitate was filtered off and washed with ethanol and then ether. The solid was purified by dissolution in dimethylformamide warmed to about 100°C, charcoaling with Norit A, and reprecipitation with ethanol to give 24 gm. (32% yield) of a deep yellow-gold product. m.p. 204° – 204.5°C. (dec.).

EXAMPLE 7 (Method C):

Preparation of N-(3-dimethylaminopropyl)-2-[3-(4-methyl-5-(N-benzylcarbamoyl)-2-thiazolyl)-2(or 1)-triazeno]-benzamide (2:1) sulfate salt To 50 gm. (0.20 mole) of 2-amino-4-methyl-5-(N-benzylcarbamoyl)thiazole dissolved in 200 ml. of 50% v/v propionic acid-glacial acetic acid and 20 ml. concentrated sulfuric acid, stirred in an ice bath, 30 ml. of isoamyl nitrite were added. The reaction mixture was poured into a stirred suspension of 44 gm. (0.20 mole) of o-amino-N-(3-dimethylaminopropyl)-benzamide in an aqueous solution of 84 gm. sodium acetate in ice water. The finely-divided red precipitate was filtered through Celite, washed with cold water and air dried. The solid was dissolved in lukewarm dimethylformamide, diluted with an equal volume of acetonitrile and then with sufficient benzene to cause precipitation. The purification is repeated to afford 14 gm. (13% yield) of an orange solid. m.p. 145°–147°C. The solid isolated by this procedure is the (2:1) sulfate salt.

EXAMPLE 8 (Method E):

Preparation of 2-[3-p-tolyl-1(or 2)-triazeno]-benzamide

To 1.36 gm. anthranilamide (0.01 mole) dissolved in 50 ml. ethanol containing 5.4 gm. 58% fluoroboric acid, and stirred in an acetone-ice bath (about -5°C), 1.5 ml. of isoamyl nitrite were added all at once. After ½ hour, the o-carbamoylbenzenediazonium tetrafluoroborate suspension was diluted with 200 ml. cold anhydrous ether. After ½ hour more, the diazonium salt (2.25 gm; 95% yield) was filtered and dried in a desiccator. dec. 131° – 133°C. (lit. 114° – 115°C.).

To 1.07 gm. of p-toluidine (0.01 mole) dissolved in 20 ml. ethanol, about 1.0 gm. of the above diazonium salt (0.004 mole) was added. The solution immediately turned orange and the product precipitated within a couple of minutes. The precipitate was filtered off, washed with ether and recrystallized foom ethanol to obtain 1.25 gm. (98% yield) of a product having a m.p. of 187° – 188°C. (dec.).

Other examples of the preparation of compounds of the formula (A) are given in Table I as follows:

TABLE I

Structure (A): benzene ring with —CONR'R'' and —N=N—NHR substituents

| EXAMPLE NO. | R | R' | R'' | m.p. °C. (dec.) | Method of Preparation | IFM* % protected |
|---|---|---|---|---|---|---|
| 1 | phenyl-CONH | H | H | 217–218° | D | 100% |
| 2 | thiazolyl | H | H | 181–182 | B, C | 80 |
| 3 | 2-Cl, 6-Me phenyl | H | H | 185–186.5 | A | 100 |
| 4 | N-ethyl carbazolyl | H | H | 192.5–193 | A | 100 |
| 5 | 4-Me-thiazolyl-CON(morpholino) | H | H | 187.5–188 | B | 100 |
| 6 | 4-Me-thiazolyl-CONHCH$_2$C$_6$H$_5$ | H | H | 204–204.5° | B, C | 100% |
| 7 | 4-Me-thiazolyl-CONHCH$_2$C$_6$H$_5$ | H | —(CH$_2$)$_3$NMe$_2$ ½ H$_2$SO$_4$ | 145–7 | C | 100$^{(a)}$ |
| 8 | 4-Me phenyl | H | H | 187–188 | A, E | 100 |
| 9 | 4-Me-thiazolyl-CONH-(2,4,6-triMe phenyl) | H | H | 190–190.5 | C | 60 |
| 10 | 2-CO$_2$Me phenyl | H | H | 186–188 | A | 80 |
| 11 | 4-Cl phenyl | H | H | 179–180 | A | 40 |
| 12 | 4-NO$_2$ phenyl | H | H | 211–213 | A | 100 |
| 13 | 2-Me phenyl | H | H | 176–178 | A | 100% |

TABLE I-continued $$\begin{array}{c}\text{CONR}^I\text{R}^{II}\\ \text{(A)}\\ \text{N=N-NHR}\end{array}$$

| EXAMPLE NO. | R | R' | R'' | (dec.) m.p. °C. | Method of Preparation | IFM* % protected |
|---|---|---|---|---|---|---|
| 14 | phenyl-Me | H | H | 179-180 | A | 80 |
| 15 | phenyl-NO₂ | H | H | 206-208 | A | 100 |
| 16 | phenyl-(Me)(Me) | H | H | 189.5-190 | A | 60 |
| 17 | Me-thiazolyl-CONH-(Cl-phenyl) | H | H | 191-191.5 | C | 60 |
| 18 | Me-thiazolyl-CONH-phenyl | H | H | 194-195 | C | 60 |
| 19 | pyridyl | H | H | 191-192 | A, B | 80 |
| 20 | quinolinyl | H | H | 216-217° | A | 40% |
| 21 | Cl-pyridyl | H | H | 187-188 | A | 40 |
| 22 | OMe-pyridyl | H | H | 186-187 | A | 100 |
| 23 | anthraquinonyl | H | H | 235-236 | A | 40 |
| 24 | phenyl-OMe (para) | H | H | 175-176 | E | 100 |
| 25 | phenyl-OMe (ortho) | H | H | 179-180 | E | 60 |
| 26 | phenyl-Me | H | Me | 154-156 | A | 100 |
| 27 | phenyl-(Cl)(Me) | H | Me | 153-154 | A | 80 |

TABLE I-continued
| EXAMPLE NO. | R | R' | R" | (dec.) m.p. °C. | Method of Preparation | IFM* % protected |
|---|---|---|---|---|---|---|
| 28 |  | H | n—Bu | 110–111° | A | 60% |
| 29 |  | H | Me | 170–172 | C | 100 |
| 30 |  | H | Et | 181–182 | C | 60[b] |
| 31 |  | Me | Me | 190–191 | C | 60 |
| 32 |  | H | Ph | 158–60 | A | 60 |
| 33 | 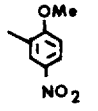 | H | H | 215–216 | A | 100 |
| 34 | 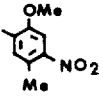 | H | H | 211–212° | A | 100% |
| 35 |  | H | H | 184–184.5 | A | 80 |
| 36 |  | H | H | 185–187 | A | 40 |
| 37 | 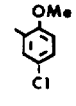 | H | H | 185–186 | A | 60 |
| 38 |  | H | H | 179–180 | A | 40 |
| 39 |  | H | H | 195–196 | A | 40% |

TABLE I-continued

| EXAMPLE NO. | R | R' | R'' | (dec.) m.p. °C. | Method of Preparation | IFM* % protected |
|---|---|---|---|---|---|---|
| 40 | [structure: Me, Cl-substituted phenyl] | H | H | 168–169 | A | 40 |

In TABLE I:
Me = CH₃; Et = C₂H₅; n—Bu = C₄H₉; and Ph = C₆H₅
*IFM - Isolated fighting mouse test at a dose of 30 mg/kg intraperitoneally; those compounds which protected at least 40% of the mice in this test were considered to be active.
**60 mg/kg intraperitoneally
***per os The most outstanding property of the triazenobenzamides of the formula (A), according to the present invention, is their highly selective abolition of aggressive behavior in doses which cause little or no signs or symptoms of central nervous system depression or toxicity.

Two models of aggression are used in the primary screening for neuroleptics, (1) isolation-induced fighting in mice (IFM), and (2) aggression induced in rats by destruction of the septal area (septal rat). Compounds are first submitted, however, to the neuropharmacological profile, a standard procedure (see, e.g., Samuel Irwin, Science, 136, 123 [1962]) employed in screening a compound to determine its usefulness as a central nervous system active compound. Those agents which cause depression over a wide dose range are then submitted to the first anti-aggression screen, the isolation-induced fighting mouse assay. As indicated in Table I, above, compounds which protect at least 40% of the mice in this test are considered to be active as anti-aggression agents.

Since they possess outstanding anti-aggressive activity in doses which cause little or no signs of central nervous system depression, the compounds of the present invention differ from known psychoactive agents, all of which cause marked depression in experimental animals. Thus, they inhibit the aggressive behavior of septal rats and inhibit isolation-induced fighting behavior in mice in doses much below those required to produce central nervous system depression or other signs of neurotoxicity.

The compounds of formula (A) of the present invention each have a neuropharmacological profile (see Samuel Irwin, Science, 136, 123 [1962]) in mice which resembles those of the major tranquilizers such as chlorpromazine. These compounds differ from chlorpromazine, however, in that each is a much weaker depressant of motor activity in the mouse.

For instance, considering the compound of Example 6, 2-[3-(4-methyl-5-(N-benzylcarbamoyl)-2(or 1)-thiazolyl)-2-triazeno]-benzamide, as shown by the data hereinafter, this compound was found to be highly selective in abolishing aggressive behavior when administered in doses which caused little or no signs of central nervous system depression or toxicity. It was found to possess some of the activities of a major tranquilizer such as chlorpromazine yet it also had one of the properties of a minor tranquilizer such as chlordiazepoxide. It was not a potent inhibitor of spontaneous motor activity in rats, nor did it produce neurotoxicity in mice or rats to the extent that chlorpromazine or chlordiazepoxide does. It was outstanding in inhibiting septal rat aggression and fighting mouse behavior.

In the latter assay the above compound was more potent that chlorpromazine or chlordiazepoxide and when one correlates the dose necessary to block aggression with that which induced neurotoxicity, it is more than two thousand times more selective in blocking aggression than chlropromazine and one thousand times more selective than chlordiazepoxide. With respect to inhibition of aggressive behavior in the septal rat, it is two hundred and twenty-two times more selective than chlorpromazine. Although this compound was effective in blocking fighting behavior in the electroshock-induced fighting mouse assay, chlorpromazine and chlordiazepoxide were almost twenty times more potent. It is still more selective than either of the latter agents, since the $NTD_{50}/ED_{50}$ ratio for the compound was 13.3 whereas with chlorpromazine or chlordiazepoxide their ratios were less than one. This is the only test in which this compound resembled chlordiazepoxide in its activity. Like chlorpromazine, this compound is virtually devoid of anti-convulsant activity. It differs from chlorpromazine, however, in that it does not protect against amphetamine aggregation-induced lethality. The compound differs significantly from chlordiazepoxide with respect to the hypothalamus, since in cats it was found that the compound had no effect on the threshold for hypothalamicinduced rage; whereas, chlordiazepoxide is specific in inhibiting this response. The compound is devoid of anti-depressant activity since it failed to (1) potentiate dihydroxyphenylalanine-induced fighting behavior in mice, and (2) antagonize tetrabenazine-induced ptosis.

The compound of Example 6 was studied in the neuropharmacological profile, which, as indicated above, is a standardized multi-dimensional observation technique used on mice to grade symptomatology and acute toxicity relative to dosage.

Loss of spontaneous motor activity accompanied by mild depression were the only symptoms observed at the 300 mg/kg dose level. A reduction in spontaneous motor activity was the only symptom observed at the 100 mg/kg dose level, whereas no dominant signs or symptoms were observed at the 30 mg/kg level. No deaths occurred at any of the dose levels. No hypothermia was observed. The results of the neuropharmacological profile indicate that this compound is a very weak central nervous system depressant.

From the IFM data in Table I, it is apparent that each of the above tested o-triazenobenzamides showed, at doses which caused little or no signs of CNS depression or toxicity, selective abolition of aggressive behavior.

2-[3-(4-methyl-5-(N-benzylcarbamoyl)-2(or 1)-thiazolyl)-2-triazeno]-benzamide, the compound of

Neurotoxicity

In the neurotoxicity test, the value ($NTD_{50}$) is defined as the dose necessary to cause 50% of mice or rats trained to walk a rotating wooden rod (5 rpm) to fall at the time of peak effect, and is a measure of drug effects on motor function or central nervous system toxicity. The results set forth in Table III were obtained when the compound of Example 6 was tested against chlorpromazine and chlordiazepoxide.

TABLE III

| | Neurotoxicity $NTD_{50}$ (mg/kg) | 95% Confidence Limits |
|---|---|---|
| I.P. | Mice | |
| Compound of Example 6 | >1280 | |
| Chlorpromazine | 0.7 | (0.4 - 1.1) |
| Chlordiazepoxide | 13.8 | (7.1 - 27.0) |
| I.P. | Rats | |
| Compound of Example 6 | ~500 | |
| Chlorpromazine | 5.3 | (3.1 - 9.1) |
| Chlordiazepoxide | 4.3 | (2.6 - 7.1) |

Example 6, was subjected to additional evaluation tests as described below.

Spontaneous Locomotor Activity

The compound of Example 6 and chlorpromazine, a commonly used major tranquilizer, were each subjected to the spontaneous locomotor activity test, in which six mice per dose were placed in individual photocell activity cages 30 minutes after i.p. (intraperitoneal) administration of the drug, for a 30 minute activity count. Table II shows the results obtained by comparing drug treated groups with control activity, $SD_{50}$ being that dose which causes a 50% reduction from control activity.

TABLE II

| Spontaneous Locomotor Activity | |
|---|---|
| | I.P. $SD_{50}$ (mg/kg) |
| | Rats |
| Compound of Example 6 | ~500 |
| Chlorpromazine | 1.7 |

The compound of Example 6 thus has a much weaker depressant action in rats in comparison with chlorpromazine.

Again, the compound of Example 6 was considerably less potent than chlorpromazine or chlordiazepoxide. In addition, the compound of Example 6 appeared to be more toxic in rats than in mice.

Anti-Agressive Activity

The compound of Example 6 was compared with chlorpromazine and chlordiazepoxide for its anti-aggressive activity. Three models of experimentally-induced aggression in rodents were studied (R. D. Sofia, Life Science, 8: 705, 1969). The results of these experiments are summarized in Table IV.

TABLE IV

| Anti-Aggressive Activity $ED_{50}$ (95% Confidence Limits) (mg/kg) i.p. Administration | | | |
|---|---|---|---|
| Agent | $ED_{50}$ | | $NTD_{50}/ED_{50}$ |
| Isolated Mouse Aggression | | | |
| Compound of Example 6 | 1.8 | (.62 - 5.22) | 710 |
| Chlorpromazine | 2.8 | (2.0 - 3.9) | 0.3 |
| Chlordiazepoxide | 20.5 | (11.3 - 37.5) | 0.7 |
| Electroshock-Induced Fighting in Mice | | | |
| Compound of Example 6 | 96.0 | (43.6 - 211) | 13.3 |
| Chlorpromazine | 5.5 | (3.1 - 9.9) | 0.1 |
| Chlordiazepoxide | 4.2 | (2.3 - 7.7) | 3.3 |
| Septal Rat Aggression | | | |
| Compound of Example 6 | ~4.5 | | 111.0 |
| Chlorpromazine | 10.7 | (4.5 - 25.7) | 0.5 |
| Chlordiazepoxide | 25.8 | (14.0 - 47.5) | 0.6 |

From these data it can be seen that the compound of Example 6 was active in antagonizing the three models of agressive behavior. It was outstanding in its ability to block aggressive behavior in the isolated mouse. It was more potent than chlorpromazine or chlordiazepoxide in this assay and when one correlates the dose necessary to block aggression with that which induces neurotoxicity, it is greater than two thousand times more selective in blocking aggression than chlorpromazine and one thousand times more selective than chlordiazepoxide. With respect to inhibition of aggressive behavior in the septal rat, it is 222 times more selective than chlorpromazine and 185 times more selective than chlordiazepoxide. Although the compound of Example 6 was effective in blocking fighting behavior in the electroshock-induced fighting mouse assay, chlorpromazine and chlordiazepoxide were almost 20 times more potent. It is still more selective than either of the latter agents, since the $NTD_{50}/ED_{50}$ ratio for the compound of Example 6 was 13.3 whereas with chlorpromazine and chlordiazepoxide their ratios were less than one.

Anti-Convulsant Activity

Anti-convulsant activity was tested according to the following procedures.

1. Maximal Electroshock Seizures ($MES_{50}$)

Groups of ten mice each were injected i.p. with a vehicle and the compound of Example 6 and placed in individual Plexiglas squares. Thirty minutes after i.p. injection, each mouse was administered an electric shock transcorneally at 50mA intensity, 0.2 seconds duration (Swinyard, et al, J. Pharmacol. Exptl. Ther., 106: 319, 1952). The criterion for activity is protection against tonic extension of the hind limbs. The dose necessary to protect 50% of the mice ($MES_{50}$) was determined. The following results were obtained.

TABLE V

| Agent | Maximal Electroshock Seizures | |
|---|---|---|
| | I.P. | $MES_{50}$ mg/kg |
| Compound of Example 6 | Inactive | (200 mg/kg) |
| Chlorpromazine | Inactive | (25 mg/kg) |
| Chlordiazepoxide | 14.3 | (8.4 – 24.3) |

The compound of Example 6, like chlorpromazine, did not protect against maximal electroshock seizures even at high doses, although chlordiazepoxide was effective in this test.

2. Pentylenetetrazol Seizures ($MET_{50}$)

In this test (modification of the method introduced by Everett and Richard, J. Pharmacol. Exptl. Ther., 81: 402, 1944), groups of ten mice each are pretreated i.p. with vehicle and various doses of the compound of Example 6 and placed in Plexiglas squares. Thirty minutes later, all mice are injected subcutaneously (s.c.) with pentylenetetrazol at 125 mg/kg and observed immediately thereafter for convulsions and death for a period of 1 hour. The dose necessary to protect 50% of the mice ($MET_{50}$) for both parameters was determined and reported in Table VI.

TABLE VI

| Agent | Pentylenetetrazol Seizures | |
|---|---|---|
| | I.P. $MET_{50}$ mg/kg | |
| Compound of Example 6 | Inactive | (200 mg/kg) |
| Chlorpromazine | Inactive | (100 mg/kg) |
| Chlordiazepoxide | 7.1 | (5.6–90) convulsions |
| | 2.6 | (2.2–3.1) death |

Neither the compound of Example 6 nor chlorpromazine exhibited anti-pentylenetetrazol activity, although chlordiazepoxide was effective.

d-Amphetamine Aggregation

Protection from d-amphetamine aggregation-induced lethality is usually afforded by alpha-adrenergic-blocking agents such as chlorpromazine, phenoxybenzamine, etc. Percent protection was determined and an $ED_{50}$ value was calculated. The results are summarized in Table VII.

TABLE VII

| Agent | d-Amphetamine Aggregation | |
|---|---|---|
| | $ED_{50}$ mg/kg | |
| Compound of Example 6 | Inactive | (200 mg/kg) |
| Chlorpromazine | 1.2 | (0.8 – 1.8) |
| Chlordiazepoxide | Inactive | (50 mg/kg) |

The compound of Example 6 and chlordiazepoxide were inactive in this procedure. Chlorpromazine was very active, probably due in part to the alpha-adrenergic blocking activity of this compound.

Drug Interaction Studies

The compound of Example 6, chlorpromazine and chlordiazepoxide were compared in the following drug interaction studies.

1. Dihydroxyphenylalanine (d2-DOPA) Fighting Test

It is well known that when monoamine oxidase inhibitors are administered prior to the administration of dl-DOPA, which is a noradrenaline precursor, convulsions or excitation occur. In this study, the MAO inhibitor pargyline (80 mg/kg) was given 1, 2 and 4 hours prior to administering 200 mg/kg of dl-DOPA. Results of this experiment are manifested by excitation, salivation, jumping, and fighting. When the compound of Example 6 (100 mg/kg), chlorpromazine (5 mg/kg) and chlordiazepoxide (15 mg/kg) were administered instead of pargyline, these symptoms were not observed. Thus, in this procedure, none of the agents tested appears to be a MAO inhibitor.

2. Antagonism of Tetrabenazine-induced Ptosis

Groups of mice were given 32 mg/kg of tetrabenazine intraperitoneally 30 minutes after an injection of the compound of Example 6 (200 mg/kg). The degree of ptosis (eyelid drooping or closure) was then determined exactly 30 minutes after tetrabenazine administration. The compound of Example 6 did not reverse tetrabenazine-induced ptosis, as do the anti-depressants desipramine or amitriptyline.

Toxicity

Table VIII gives the results of 5 day lethality studies following single injections of drug. All values presented represent tests conducted when animals were housed 10 per cage. The compound of Example 6 was compared with chlorpromazine and chlordiazepoxide. In these and all the preceding calculations, the method of Litchfield and Wilcoxon (J. Pharmacol. Exptl. Ther., 96: 99, 1949) was used to estimate effective ($ED_{50}$) or lethal ($LD_{50}$) dose.

TABLE VIII

| Agent | $LD_{50}$ (95% Confidence Limits) mg/kg | | |
|---|---|---|---|
| | Mice | | Rats |
| | I. P. | P. O. | I. P. |
| Compound of Ex. 6 | >1280 | >800 | >1400 |
| Chlorpromazine | 136 | 280 | 138 |
| | (106–174) | (187–418) | (133–141) |
| Chlordiazepoxide | 400 | 810 | 265 |
| | (265–604) | (688–958) | (224–313) |

These data show that the compound of Example 6 is much less toxic than chlorpromazine or chlordiazepoxide when administered i.p. or orally to mice and rats.

In addition to the above tests conducted on the compound of Example 6, the compounds of Examples 3 and 7 (each of which protected 100% of the test animals in the IFM test) were subjected to additional testing. The test data are given below.

| Compound | Neurotoxicity Rotorod Determination Dose | Animal | Route | % Successful |
|---|---|---|---|---|
| Compound of Example 3 | 30 mg/kg | rat | P. O. | 100 % |
| Compound of Example 7 | 80 mg/kg | rat | P. O. | 100 % |
| Compound of Example 7 | 100 mg/kg | mouse | I. P. | 100 % |
| Compound of Example 7 | 100 mg/kg | mouse | P. O. | 100 % |

These data indicate that the compounds of Examples 3 and 7 do not cause depression and have $NTD_{50}$ values greater than 100.

In the isolated fighting mouse aggression test, the compounds of Examples 2, 3, 5, 10, 33, 34 and 35 were found to have the following $ED_{50}$ values (i.p. administration):

| Compound of Example No. | $ED_{50}$ (IFM) mg/kg | |
|---|---|---|
| 2 | 9.4 | (6.27–14.1) |
| 3 | 9.1 | (6.89–12.56) |
| 5 | 6.7 | (5.23–8.40) |
| 10 | 6.0 | (4.34–8.30) |
| 33 | 14.0 | (7.86–24.9) |
| 34 | 14.5 | (8.3–25.8) |
| 35 | 5.2 | (1.8–15.1) |

In the septal rat aggression test, the compound of Example 7 was found to give 100% protection at both 6.25 mg/kg and 12.5 mg/kg i.p., indicating an $ED_{50}$ of less than 6.25 mg/kg.

Evoked Hypothalamic Rage Response - Cats

The effect of the compound of Example 6 on the hissing response elicited by hypothalamic stimulation in cats was studied in an effort to determine if it had properties similar to that of chlordiazepoxide and other anti-anxiety-like agents. Chlordiazepoxide has been shown by Baxter, Life Sciences, 3: 531, 1964, to increase the threshold of the hypothalamus to electrical stimulation. Cats with chronically implanted electrodes, stereotaxically placed in the perifornical region of the hypothalamus, were used in this study. Stimulation was accomplished in the unanesthetized, freely moving animal, and the threshold for the hissing response was determined with the following stimulus parameters: square wave stimulation of 150 Hz with a duration of 0.5 msec and voltage ranging from 5.4 to 30. The compound of Example 6 was administered orally in capsule form. Following administration, the stimulation threshold for the hiss response was determined at 1, 2, 4, 6 and 24 hours. If an effect was observed, the stimulation was carried out daily until the thresholds returned to control values. The compound of Example 6 was administered orally at a dose of 25 mg/kg for three days. The compound of Example 6 had no effect on hypothalamic stimulation. The rage response was not changed in intensity or character and the delay from stimulus to response was not changed. A few measurements were made in an effort to establish if this compound decreased the threshold for the rage response, but this effect was not observed during the experiments. It can be concluded that the compound of Example 6 has no effect on hypothalamic excitability in cats and in this respect differs markedly from chlordiazepoxide.

The compounds of the present invention, either alone or in the form of a pharmaceutical composition, may be administered to an animal subject in any of a number of forms and via any of several routes. Thus, the compounds or compositions thereof may be orally administered in the form of tablets, pills, or capsules, or in the form of a solution or liquid suspension. They may also be administered in the form of a parenteral suspension or solution. The compounds or compositions thereof may also be administered rectally, in the form of a suppository.

When orally administering the compounds of compositions, use can be made of a tablet, pill or capsule consisting entirely of one of the desired compounds, although ordinarily a composition comprising an effective amount of the compound and varying amounts of one or more physiologically inert materials such as carriers, vehicles, binders and the like will be used. Additionally, the compounds may be orally administered in the form of a suspension thereof in a suitable vehicle such as a syrup.

When parenterally administering the compounds or compositions, use may be made of a parenteral solution or suspension of the compounds in a suitable solvent or suspension medium.

The compounds and compositions of the present invention may also be administered rectally in the form of a suppository comprising an effective amount of the desired compound and a suitable vehicle such as petroleum jelly.

The following examples are specific formulations of compositions according to the invention:

EXAMPLE 41:

Tablets may be prepared by the compression of a wet granulation containing the following:

| Ingredients | In each |
|---|---|
| 2-[3-(4-methyl-5-(N-benzylcarbamoyl)-2-thiazolyl)-2(or 1)-triazeno]-benzamide | 25 mg. |
| Polyvinylpyrrolidone | 6 mg. |
| Lactose | 25 mg. |
| Alcohol, 3A, 200 proof | 1 ml. |
| Stearic Acid | 3 mg. |
| Talc | 4 mg. |
| Corn Starch | 15 mg. |
| Dosage: 1 tablet 3 times a day. | |

EXAMPLE 42:

A liquid suspension for oral administration may be prepared in the following formulation:

| Ingredients | In each 5 cc. |
|---|---|
| 2-[3-(4-methyl-5-(N-benzylcarbamoyl)-2-thiazolyl)-2(or 1)-triazeno]-benzamide | 25 mg. |
| Sodium carboxymethylcellulose | 5 mg. |
| Syrup USP | 5 cc. |
| Dosage: 1 teaspoonful (5 cc.) every 3 to 4 hours. | |

EXAMPLE 43:

Dry filled capsules (DFC) consisting of two sections of hard gelatin may be prepared from the following formulation:

| Ingredients | In each |
| --- | --- |
| 2-[3-(4-methyl-5-(N-benzylcarbamoyl)-2-thiazolyl)-2(or 1)-triazeno]-benzamide | 25 mg. |
| Lactose USP | q.s. |
| Dosage: 1 capsule 3 times a day. | |

EXAMPLE 44:

A parenteral suspension for intra-muscular administration may be prepared in the following formulation:

| Ingredients | In each |
| --- | --- |
| 2-[3-(4-methyl-5-(N-benzylcarbamoyl)-2-thiazolyl)-2(or 1)-triazeno]-benzamide | 10 mg. |
| Isotonic solution (0.85% saline) | 5 cc. |
| Surfactant (a 1% solution of polysorbate 80 USP) | 1 cc. |
| Dosage: Inject 1 cc. when needed. | |

EXAMPLE 45:

A suppository capsule may be formulated as below:

| Ingredients | In each |
| --- | --- |
| 2-[3-(4-methyl-5-(N-benzylcarbamoyl)-2-thiazolyl)-2(or 1)-triazeno]-benzamide | 25 mg. |
| Cocoa butter | q.s. |
| Dosage: 1 suppository every 3 to 4 hours. | |

Variations can, of course, be made without departing from the spirit and scope of the invention.

Having thus described our invention, what we desire to secure by Letters Patent and hereby claim is:

1. A method of preventing and/or inhibiting aggressive behavior in an animal subject, said method comprising administering to an animal subject a therapeutically effective amount of a compound of the formula:

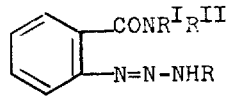

wherein R is

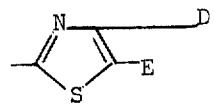

in which D is hydrogen or methyl and E is hydrogen or

wherein F is hydrogen and G is phenyl, halophenyl, trimethylphenyl or benzyl; or F and G together with the nitrogen atom to which they are bonded, form a morpholine ring;

$R'$ is hydrogen or methyl and $R''$ is hydrogen, lower alkyl, phenyl or the sulfate of a dimethylamino lower alkyl group.

2. The method of claim 1, wherein R is:

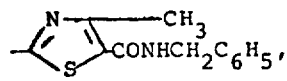

and $R'$ and $R''$ are both hydrogen.

3. The method of claim 1, wherein R is

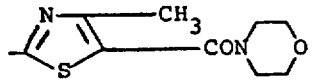

and $R'$ and $R''$ are both hydrogen.

4. The method of claim 1, wherein R is

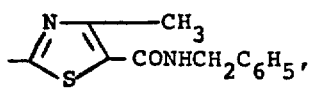

$R'$ is hydrogen and $R''$ is $-(CH_2)_3-N(CH_3)_2$. ½ $H_2SO_4$.

* * * * *